United States Patent [19]

Klock et al.

[11] Patent Number: 4,951,504
[45] Date of Patent: Aug. 28, 1990

[54] PROCESS AND APPARATUS FOR TESTING THE AXLES AND/OR SPRINGS AND/OR ADJACENT COMPONENTS OF COMMERCIAL VEHICLES

[75] Inventors: Jürgen Klock, Otzberg; Gerhard Fischer, Darmstadt; Vatroslav Grubisic, Reinheim, all of Fed. Rep. of Germany

[73] Assignee: Fraunhofer-Gesellschaft Zur Forderung Der Angewandten Forschung E.V, Fed. Rep. of Germany

[21] Appl. No.: 377,470

[22] Filed: Jul. 10, 1989

[30] Foreign Application Priority Data

Jul. 13, 1988 [DE] Fed. Rep. of Germany ....... 3823764

[51] Int. Cl.$^5$ ........................................... G01M 19/00
[52] U.S. Cl. .................................................. 73/118.1
[58] Field of Search ................ 73/117.1, 118.1, 865.3, 73/865.6, 865.8, 865.9, 11

[56] References Cited

U.S. PATENT DOCUMENTS

| 3,877,288 | 4/1975 | Schiefen | 73/11 |
| 4,133,201 | 1/1979 | Klinger | 73/12 |
| 4,501,139 | 2/1985 | Petersen | 73/118.1 |
| 4,898,026 | 2/1990 | Damitz | 73/118.1 |

FOREIGN PATENT DOCUMENTS 388206  6/1973 U.S.S.R. ............................. 73/865.9

OTHER PUBLICATIONS

"ATZ Automobiltechnische Zeitschrift", 74 (1972), 4, pp. 139–145.

"VDI Berichte", No. 632, 1987, pp. 1, 25–28, 33–37.

Primary Examiner—Robert Raevis
Attorney, Agent, or Firm—Ostrolenk, Faber, Gerb & Soffen

[57] ABSTRACT

The invention provides a process and an apparatus for testing commercial vehicle axles and/or springs and/or components adjacent thereto under load conditions resembling those occurring in practice. An entire commercial vehicle axle with two commercial vehicle springs and original attachment parts are tested by the introduction of low frequency deformations of vertical forces into a supporting assembly and of lateral forces, longitudinal forces and high frequency vertical wheel forces in each case into a wheel substitute or wheel or a brake force transmitting lever. In the course of this test, the supporting assembly is tilted about a pivot shaft or pivot axis which is displaceable in the vertical direction so that the axle of the commercial vehicle remains parallel to the horizontal. Vertical spring excursions and tilting of the supporting assembly are brought about by two vertical force generators which act on the supporting assembly and produce forces of reaction at the point of contact of the wheel tread with the vertical support. For testing the springs of the commercial vehicle alone, only one lateral force generator is used instead of two; and for the introduction of braking and driving forces and/or longitudinal forces, only one braking and driving force generator is used instead of two and, respectively, only one longitudinal force generator instead of two. The single force generator then acts at the center of the axle by way of a force transmitting means which is fixed to the right and the left wheel substitute or the right and left brake force transmitting lever.

11 Claims, 4 Drawing Sheets

PROCESS AND APPARATUS FOR TESTING THE AXLES AND/OR SPRINGS AND/OR ADJACENT COMPONENTS OF COMMERCIAL VEHICLES

BACKGROUND AND SUMMARY OF THE INVENTION

This invention relates to a process and an apparatus for testing commercial vehicle parts such as axles and/or springs and/or one or more other components adjacent thereto. The parts are subjected by means of at least one vertical force generator to vertical forces of the type occurring when a commercial vehicle is in use while the spring of the commercial vehicle is fixed by means of a supporting assembly at that one or more points of attachment corresponding to the point or points at which it is attached to the body of the commercial vehicle.

The spring suspension of commercial vehicles has the function of compensating for irregularities on the ground and absorbing the forces transmitted from the roadway. Furthermore, the axle is guided by means of leaf springs so that all the forces transmitted from the wheel into the axle are introduced into the frame by way of the springs. A reliable test for strength in test stands taking into account all types of loads under loading conditions simulating those occurring in practice is therefore of the utmost importance.

The loads to which commercial vehicle springs are subjected will first be described with reference to FIGS. 1 and 2:

The loads on commercial vehicle springs are produced by the following forces resulting from irregularities on the ground and driving maneuvers:

Vertical forces $F_V$

Lateral forces $\pm F_S$

Longitudinal forces $\pm F_L$

Braking and driving forces $\pm F_B$

Figure 1:
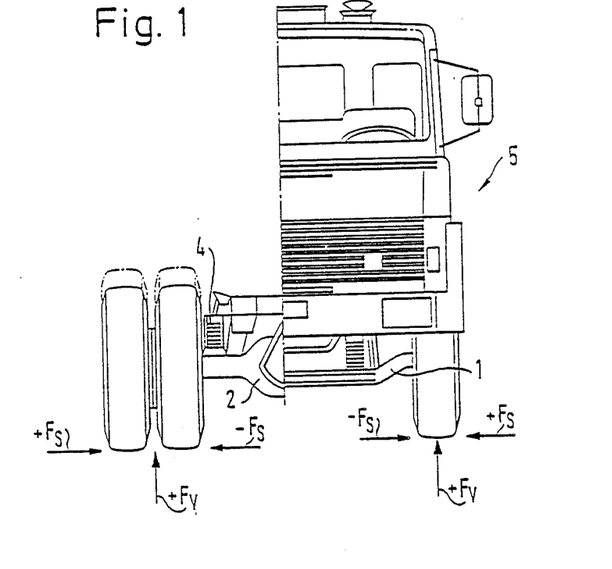
FIG. 1 is a front view of a commercial vehicle with parts omitted from the left side for the sake of clarity of the drawing.
Figure 2:
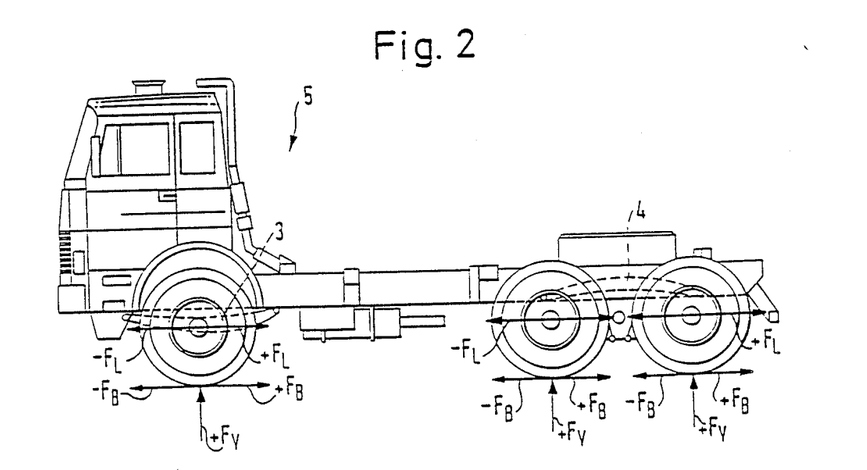
FIG. 2 is a side view of the commercial vehicle of FIG. 1, also with parts omitted.

These forces acting on the front axle spring 3 through the front axle 1 and the rear axle spring 4 through the rear axle 2 of the commercial vehicle 5 are entered in FIGS. 1 and 2 and have the following causes and significanes:

(a) Vertical forces $F_V$: The vertical forces $F_V$ result from the static preload due to the weight of the vehicle itself, quasi-static weight displacements on cornering, with compression of one of the two vehicle springs while the other is under expansion, quasi-static weight displacements with symmetric spring compression on braking, dynamic forces occurring simultaneously on both sides on travelling over elevations in the ground, transverse grooves, rails or the like, and accidental loads when driving over irregularities in the ground. The latter are relatively high frequency loads which occur on both sides of the vehicle independently of one another.

(b) Lateral forces $\pm F_S$: Quasi-static lateral forces act during cornering, positive lateral forces $+F_S$ acting from the wheels on the outside of the curve towards the center of the vehicle while negative lateral forces $-F_S$ act from the wheels on the inside of the curve towards the outside of the vehicle. High frequency dynamic lateral forces occur when the vehicle travels over irregularities on the ground and potholes; in such cases, the direction of action on each wheel may extend alternately in both directions so that both positive and negative lateral forces $\pm F_S$ occur.

(c) Longitudinal forces $\pm F_L$: High frequency longitudinal forces $\pm F_L$ act at the center of the axle stub both in the rearward direction as positive longitudinal forces $+F_L$ and in the forward direction as negative longitudinal forces $-F_L$. They constitute the horizontal component of any impact transmitted obliquely into the rotating wheel such as occurs when the vehicle travels over irregularities in the ground.

(d) Braking and driving forces $\pm F_B$: Braking forces $+F_B$ and driving forces $-F_B$ act on the contact surface of the wheel tread as a result of a driving maneuver and in accordance with the maneuver carried out.

Vertical forces, lateral forces, longitudinal forces and driving and braking forces may also occur as a reaction to asymmetric deformation of the frame, asymmetric spring excursions and cornering.

The overall deformations of springs of commercial vehicles listed below result from the co-operation of the forces described above:

(1) Symmetric and asymmetric spring excursions due to vertical forces $F_V$ acting on the wheel.

(2) Twisting about the longitudinal axis due spring excursions (moment about the longitudinal axis).

(3) Lateral displacement due to lateral forces $\pm F_S$ and possibly also twisting.

(4) S-deformation due to braking and driving forces $+F_B$ (5) Longitudinal stress produced by longitudinal forces $\pm F_L$ in combination with spring excursions or S-impact.

(6) Twisting about the vertical axis due to differential braking or longitudinal forces.

To explain the state of the art of testing commercial vehicle springs and the difficulties inherent in the testing technique hitherto available, reference will now be made to FIGS. 1 to 4 and the documents cited below which show several test stands for carrying out such tests and illustrate schematically the difference between the testing technique hitherto available and the actual conditions prevailing when commercial spring vehicles are under load on the road:

(1) Betriebslastensimulation an Fabrzeugbauteilen mittels servohydraulischer Prüufeinrichtungen (Operational Load Simulation on Vehicle Parts by means of Servohydraulic Test Devices), G. Jacoby, SCHENCK in: VDI-Berichte No. 632, 1987, FIG. 18.

(2) Simulation von Betriebsbeanspruchungen für den Lebensdauernachweis von Leichtbaublattfedern (Simulation of Operational Stresses for Testing the Service Life of Lightweight Leaf Springs), H. Oppermann and D. Schütz FhG-Berichte 2/3, 1987, pages 23–29.

(3) Prüfung im Automobilbau, (Testing in the Manufacturing of Automobiles), G. Jacoby, from the Lecture entitled "Prüfung von Werkstoffen und Maschinenbauteilen mittels programmierbarer elektrohydraulischer Prüfmaschinen"; (Testing of Materials and Machine Parts by means of Programmed Electrohydraulic Test Machines), Prague, 28–30.11.1984, CARL SCHENCK AG.

Reference will first be made to a test stand in which the hitherto most widely practiced testing technique is carried out. In this test stand, a leaf spring of a commercial vehicle is fixed to the test stand by its two longitudinal ends at which it is normally connected to the car body when it is in the assembled vehicle while a vertical force generator acts as the only force generator of the test stand on that point at which the axle is normally connected in the assembled commercial vehicle. This hitherto most widely used testing technique thus takes into account only the simulation of vertical spring excursions. It is not possible by these means to obtain any reliable information on the service life of the commercial vehicle spring since the other loads occurring in practice are not accounted for.

Figure 3:
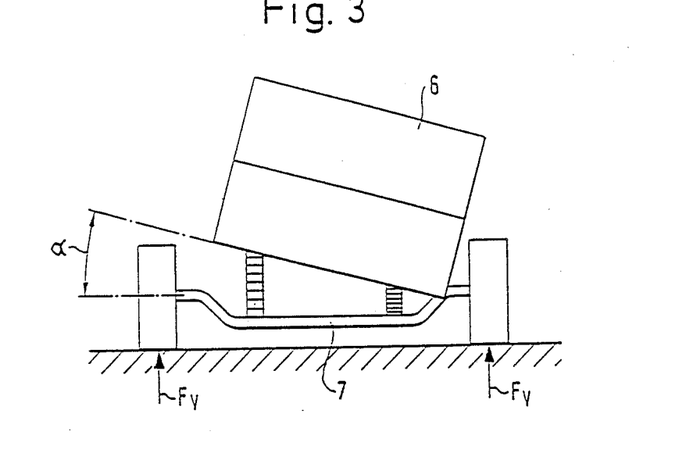
FIG. 3 is a diagram illustrating the compression and expansion of the springs as they occur in practice in a commercial vehicle.
Figure 4:
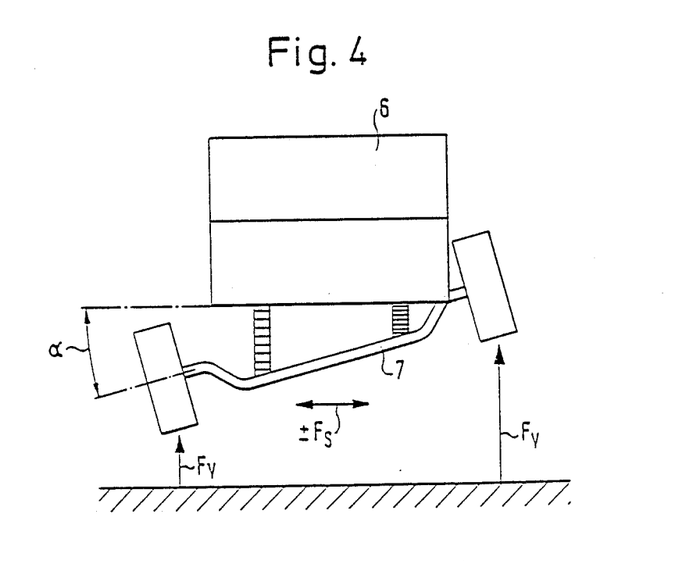
FIG. 4 is a diagram illustrating the compression and expansion of the springs as they occur in the known test stands discussed above.

The test stand illustrated in FIG. 18 of Document 1 for simultaneously testing two leaf springs which are rigidly connected together at the points at which they are normally connected to the axle comprises two vertical force generators, a lateral force generator and a braking force generator. Such a test stand may therefore be used to simulate lateral forces and braking forces in addition to vertical forces but it is less suitable for simulating the complex forces to which leaf springs are subjected to load conditions on the road, the reasons for this being as follows:

(a) Since the leaf springs are fixed at their longitudinal ends in the test stand, the forces acting on them are not a true reflection of the conditions prevailing in practice. This falsification will now be explained with reference to FIGS. 3 and 4, FIG. 3 indicating schematically the conditions occurring in practice under driving conditions while FIG. 4 shows the conditions in the test stand of FIG. 18 of Document 1. Since the longitudinal ends of the leaf spring are in practice fixed to the body 6 of the vehicle while the longitudinal centers of the springs are fixed to the axle 7, testing of the leaf springs in the test stand shown in FIG. 18 of Document 1 amounts to a reversal of the conditions occurring in practice since the car body 6 in the test stand remains parallel to the horizontal, which corresponds to the roadway, as shown in FIG. 4, whereas under practical driving conditions, for example when the vehicle is cornering, the car body 6 together with the frame is inclined to the horizontal or the roadway, as shown in FIG. 3, and the axle 7 remains virtually parallel to the roadway, apart from any inclination due to compression of the tires.

Considerable falsifications occur in the test stand shown in FIG. 18 of Document 1 due to the force generators acting on the axle substitute construction. This manner of introducing loads and the oblique positioning of the axle substitute construction, which corresponds to oblique positioning of the whole axle 7 of FIG. 4 in relation to the roadway, causes the directions of action of the vertical forces $F_V$, the L lateral forces $\pm F_S$ and the braking forces $\pm F_B$ to be falsified to such an extent that large errors and coupling faults may occur. In contrast to the situation occurring in practice, in which the axle remains virtually parallel to the roadway and the vertical forces are introduced at right angles to the axle and the lateral forces parallel to the axle (see FIG. 3), the situation found in the test stand of FIG. 18 of Document 1 is that, in contrast to the conditions occurring in practice, the vertical forces are introduced in a direction which is not perpendicular to the vehicle axle and the lateral forces are introduced in a direction which is not parallel to the axle, as may be seen from FIG. 4.

(b) Since all the force generators in the test stand shown in FIG. 18 of Document 1 act on the axle substitute construction, the vertical forces, lateral forces and braking forces cannot be introduced independently of one another and therefore influence one another, all the more so when the axle is set obliquely, as discussed with reference t FIG. 4.

(c) Since the test stand shown in FIG. 18 of Document 1 is equipped with only one lateral force generator and one braking force generator, it cannot simulate the lateral forces and braking forces which in practice act independently of one another on both sides of the axle of the vehicle.

(d) The vertical forces produce large spring excursions, so that high test frequencies which would correspond to frequencies occurring in practice cannot be achieved.

There still remains to be mentioned the test stand described in Document 2, which is designed for testing the strength of individual leaf springs and not for testing the whole assembly comprising wheel, axle and springs.

In test installations for testing vehicle axles subjected to multi-axial introduction of forces, the axle is either fitted into the complete vehicle or mounted in a test frame. The principles on which this is carried out are illustrated for passenger vehicles in Document 1, FIGS. 23 to 26, and for trucks and lorries in Document 3, FIGS. 63 to 67.

Common to all these test installations is that the wheel forces act against the mass of the vehicle, which may be either locked in position or free to move but which, in contrast to conditions occurring on the road, remains largely in position while the roadway must be inclied. In this case, as also in the spring test stand illustrated in Document 2, the force generators must simulate the entire spring excursions, with the result that both the frequency of testing which can be attained and the quality of simulation when testing the complete axles are impaired. It is therefore necessary to compensate for the influence of the force components on one another by means of an elaborate electronic correction of the geometry.

It is an object of the present invention in particular to provide a process and an apparatus for testing commercial vehicle axles and springs whereby the components of the axle can be tested under loading conditions similar to those occurring in practice, thereby eliminating the above mentioned, in some cases serious disadvantages of known test apparatus.

The process according to the invention for testing the axles or springs of commercial vehicles, in which the commercial vehicle axle or spring is subjected to vertical forces of the type occurring when a commercial vehicle is in use while the axle or spring is held by a supporting assembly at the point or points of attachment by which said axle or spring is normally attached to the body of the commercial vehicle, is distinguished according to the invention in that for testing the axle and/or spring of a commercial vehicle and/or one or more other, adjacent components under loading conditions similar to those occurring in practice, the supporting assembly is mounted to be moveable and the axle and/or spring and/or other component(s) of the commercial vehicle is or are subjected by way of the moveable supporting assembly to at least those vertical forces which correspond to a static and/or low frequency loading of the commercial vehicle axle and/or spring and/or other component(s) while those parts of the commercial vehicle axle through which wheel forces are introduced in the vertical direction of action are kept substantially fixed in position or only moved with vertical forces of a magnitude which correspond to a relatively high frequency loading of the axle and/or spring and/or other component(s) of the commercial vehicle. The vertical forces corresponding to a static and/or low frequency loading of the commercial vehicle axle or spring are those vertical forces which bring about the main excursions of compression and expansion of the commercial vehicle springs, which are followed by the movement of the supporting assembly.

This arrangement always enables the vertical forces to be introduced in the same manner as occurs under driving conditions regardless of the degree to which the springs of the vehicle are compressed so that the corresponding falsifications discussed above are avoided. The resulting spring excursions are small and in particular a vertical force preload may be produced on which a low frequency and/or relatively high frequency vertical force load may be superimposed. These and other advantages are described in more detail below.

As a further development of the invention, there is provided a process in which, instead of or in addition to being subjected to vertical forces, the axle and/or spring and/or other component(s) of the commercial vehicle is or are subjected to lateral forces and/or longitudinal forces and/or braking or driving forces of the kind occurring when a commercial vehicle is in use. These forces are introduced either through those points of attachment of the vehicle spring which correspond to its attachment to the axle of the vehicle and/or through the axle of the vehicle itself. This further development is distinguished according to the invention in that for testing the spring of the commercial vehicle and/or the axle connected thereto and/or the other component(s) under load conditions resembling those occurring in practice, the lateral forces and/or longitudinal forces and/or braking or driving forces are introduced into the axle and/or spring and/or other component(s) of the commercial vehicle by way of the commercial vehicle axle connected to the spring or by way of at least one wheel or wheel substitute connected to the commercial vehicle axle and optionally by way of a brake force transmitting lever.

A further feature of the process according to the invention is distinguished in that for testing the axle of the commercial vehicle and/or two commercial vehicle springs and/or the other component(s) under loading conditions resembling those occurring in practice, at least two commercial vehicle springs are held by the supporting assembly, preferably in the manner in which they are fixed to the body of a commercial vehicle when in use, most preferably by means of original parts connected to the commercial vehicle axle which is provided on each side with wheels or wheel substitutes, optionally in each case in combination with a brake force transmitting lever.

Under these conditions, the axle of the commercial vehicle can be held fixed in the direction of spring compression and expansion apart from vertical displacements which are small compared with the maximum excursion of compression and expansion of the commercial vehicle spring(s), in particular less than 10%, preferably less than 5% of the mentioned maximum excursion of the spring. This corresponds to real operating conditions to a high degree.

The supporting assembly may be mounted to pivot about a pivot shaft which is capable of parallel displacement in the direction of spring excursion and which preferably extends in a direction perpendicular to the direction of spring excursion and perpendicular to the axial direction of the vehicle axle.

When the process is carried out with two commercial vehicle springs, the pivot shaft may be guided to undergo parallel displacement along a straight line which is equidistant at every point to the two commercial vehicle springs.

Further, the pivot shaft is preferably held in the plane in which the vehicle spring is fixed, in particular in the plane of the spring bushes or brackes, plus or minus the height of the commercial vehicle springs, when the supporting assembly is in the load free or statically loaded state.

Particularly short spring excursions of compression and expansion are obtained when the vertical forces act in the line of action or close to the line of action of the commercial vehicle spring or springs.

Furthermore, when the process is carried out with two commercial vehicle springs, the vertical forces may be arranged to act on the supporting assembly in such a manner that when they act simultaneously, they give rise to symmetric compression of both commercial vehicle springs, and when they act alternately, they give rise to compression of one spring with simultaneous expansion of the other spring. For testing two commercial vehicle springs alone, the lateral force and the braking or driving force may be introduced between the ends of the commercial vehicle axle, in particular centrally between the two ends of the axle, in each case by way of a force transmitting means extending from the point of introduction of the force to the wheel or wheel substitute or the brake force transmitting lever of the one or other end of the axle, and longitudinal forces need only be introduced at one point. Lastly, relatively high frequency vertical forces may be introduced into the axle and/or spring(s) and/or other component(s) of the commercial vehicle by way of the vehicle axle, in particular by way of at least one wheel or a wheel substitute connected to the axle or a brake force transmitting lever attached thereto.

The apparatus for testing commercial vehicle axles and/or springs provided by the invention is distinguished according to the invention in that for testing the axle and/or spring and/or other component(s) of the commercial vehicle under loading conditions resembling those occurring in practice, the supporting assembly is mounted to be moveable and the moveable assembly is coupled to at least one vertical force generator for producing at least vertical forces of the kind corresponding to a static and/or low frequency loading of the commercial vehicle axle and/or spring while that point of attachment of the commercial vehicle spring which corresponds to its point of attachment to the axle of the commercial vehicle and/or that point on the commercial vehicle axle through which the wheel forces are introduced is/are held in a substantially fixed position in the direction of action of the vertical force generator or are moveable by means of a further vertical force generator which, however, produces only those vertical forces which correspond to a relatively high frequency loading of the commercial vehicle axle and/or spring(s) and/or other component(s).

This apparatus is preferably so designed that the supporting assembly is mounted to pivot about a preferably horizontal pivot shaft. Further, the pivot shaft is guided for parallel displacement by means of at least one, preferably vertical guide. In particular, the pivot shaft may be guided by one guide on each side of the supporting assembly.

It is particularly advantageous to arrange the pivot shaft so that when the supporting assembly is coupled to at least state, the shaft lies in the plane containing the means for fixing the commercial vehicle springs, in particular the spring bushes or brackets, plus or minus the height of the load free commercial vehicle springs.

According to a particularly preferred embodiment of the invention, the supporting assembly is coupled to at least two vertical force generators arranged so that the points of their connection to the supporting assembly are arranged symmetrically with respect to the pivot shaft. The vertical force generator or generators may be coupled to the supporting assembly in such a manner that the connecting points lie in the line of action of the spring or springs of the commercial vehicle.

Further developments of the invention are stated in the subclaims to which specific reference is made here as disclosure of further features of the invention.

BRIEF DESCRIPTION OF THE DRAWINGS

The invention will now be described with the aid of a particularly preferred embodiment described with reference to the drawings, in which.

DETAILED DESCRIPTION

Figure 5:
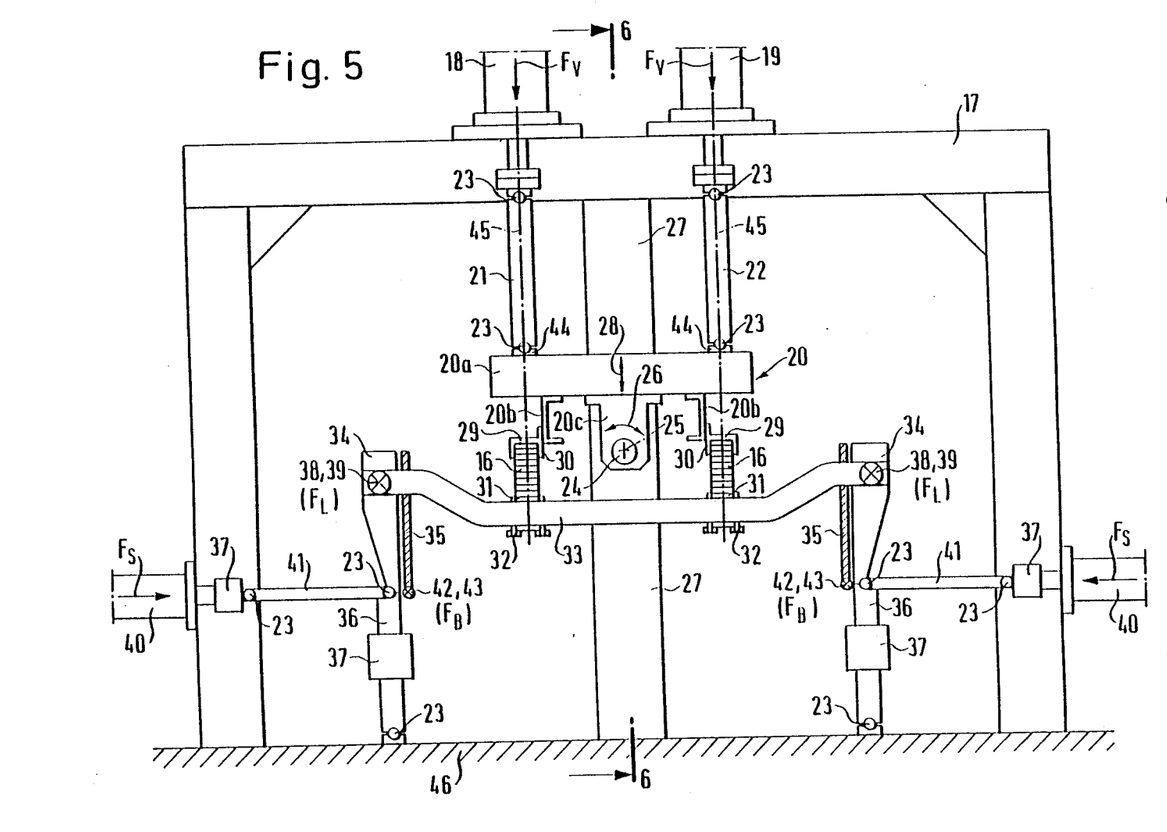
FIG. 5 is an elevational view of an embodiment apparatus according to the invention for testing the axle and/or springs and/or adjacent components of commercial vehicles.
Figure 6:
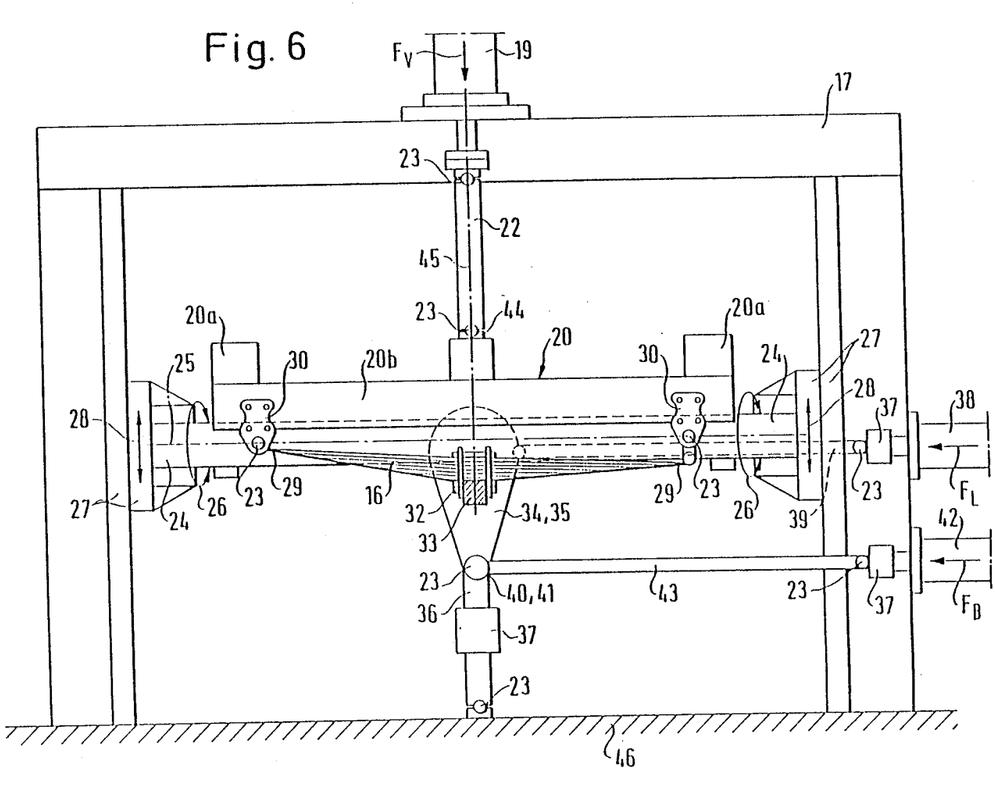
FIG. 6 is a view of the embodiment of the apparatus according to the invention taken on the line A—A of FIG. 5.

A detailed description will now be given of FIGS. 5 and 6 showing the apparatus for testing commercial vehicle springs 16, comprising a frame, stand, supporting structure or the like 17 which is so designed that the springs 16 of the commercial vehicle are subjected to vertical forces $F_V$ of the type which occur in practice when the vehicle is in operation. These vertical forces $F_V$ are produced by means of vertical force generators 18 and 19.

In the embodiment illustrated, the vertical force generators 18 and 19 are mounted in the upper part of the frame 17 in such a manner that the vertical forces $F_V$act in a vertical direction as this provides the most advantageous arrangement for testing the vehicle springs 16 and the whole arrangement but it should be pointed out that it would be possible in principle to arrange the vertical force generators 18 and 19 and indeed the whole apparatus in a position other than that shown in FIGS. 5 and 6, in fact any position corresponding to a rotation of FIGS. 5 and 6 in the plane of the drawing. Although not all these positions are advantageous, the invention covers all these possibilities, especially also the possibility of arranging the vertical force generators 18 and 19 horizontally as, for example, in the known apparatus disclosed in Document 1. If, therefore, the directions and arrangements of the parts of the apparatus of FIGS. 5 and 6 are described in this text as horizontal, vertical or the like, it should be noted that these are only preferred directions to which any angle equal for all directions could in principle be added, in particular an angle of 90°. It should also be noted that even in the arrangement shown in FIGS. 5 and 6, the vertical force generators 18 and 19 could be arranged in the lower region of the frame 17 or the region of the base 46, but this arrangement is not particularly advantageous because the attachment to the vehicle springs 16, which in the present case are leaf springs, by means of the supporting assembly 20 described below would then be somewhat more difficult and the space for accommodating the vertical force generators 18 and 19 is relatively restricted in the lower region. Each of the two vertical force generators 18 and 19 is coupled to the supporting assembly 20 by way of a force transmitting rod 21 or 22, respectively, with interposed joints 23. The said supporting assembly 20 comprises an auxiliary frame 20a, a longitudinal frame 20b and a bearing or support 20c for a pivot shaft, all these parts being rigidly and firmly connected together.

A pivot shaft 24 is mounted in the pivot shaft bearing 20c, as implicit in these terms. This pivot shaft 24 extends horizontally and together with the pivot bearing 20c it forms a pivot joint for the supporting assembly 20 so that the said assembly 20 is capable of tilting or pivoting about the axis 25 of the pivot shaft 24, as indicated by the double arrows 26 in FIGS. 5 and 6.

The pivot shaft 24 is supported by a linear guide 27 at each end to enable it to execute parallel movements in a vertical direction. These linear guides 27 are preferably vertical supports on opposite sides of the frame 17, as illustrated. The parallel displaceability of the pivot shaft 24 in the vertical direction is indicated by double arrows 28 in FIGS. 5 and 6.

The supporting assembly 20 is thus mounted or guided so as to be simultaneously tiltable about a horizontal axis 25 and displaceable parallel to itself in a vertical direction. Although this method of moveably mounting and guiding the supporting assembly 20 is particularly to be preferred, as has been demonstrated by investigations and experiments which have led to the invention, the latter is by no means restricted to this special arrangement for moveably mounting and guiding the supporting assembly but in principle covers all moveable guides and bearing for the supporting assembly 20 which enable the assembly to absorb the compressions and expansions of one or more commercial vehicle springs 16, in particular in the manner in which they occur when such vehicle springs 16 are under load conditions resembling those occurring in practice.

While the vertical force generators 18 and 19 are coupled to the upper end of the supporting assembly 20, the commercial vehicle springs 16 are fixed to the lower part of the supporting assembly 20, i.e. in the present case to the longitudinal frame 20b. They are attached, for example, by means of spring brackets 30, at those points of attachment 29 by which they are normally attached to the body of the vehicle when in use.

At their points of attachment 31, which are opposite to their points of attachment 29 and correspond to the points at which they are connected to the axle of the commercial vehicle, the two springs 16 are fixed to a commercial vehicle axle 33 by means of suitable fixing devices 32 such as spring bushes. One wheel substitute 34 and one brake force transmitting lever 35 are mounted at each end of this commercial vehicle axle 33, the wheel substitute 34 being rotatable and the brake force transmitting lever 35 rotationally fixed on the axle 33 in conventional manner known per se.

The commercial vehicle axle 33 is positionally substantially fixed in the vertical direction. The term "substantially" is used here to mean that the far greater excursions of compression and expansion of the commercial vehicle springs 16 are absorbed by the movement of the supporting assembly 20 while the axle 33 either remains stationary or undergoes only slight vertical movements as a result of absorbing correspondingly slight vertical movements which may occur under driving conditions due to high frequency or relatively high frequency vertical force loads produced, for example, by impacts due to irregularities in the ground. The commercial vehicle axle 33 is, however, indeed virtually fixed in the vertical direction when such high frequency or relatively high frequency vertical loads are transmitted to the vehicle springs 16 by way of the supporting assembly 20 in addition to the static and/or low frequency vertical force loads which produce the main spring excursions of compression and expansion or when there just happen to be no high frequency or relatively high frequency vertical loads acting on the system. The means by which the axle 33 is kept positionally fixed in the vertical direction consist of a vertical support 36 on each side mounted by means of joints 23 and connected to the wheel substitute 34 of that side by which it supports the corresponding end of the vehicle axle 33.

Each of the two vertical supports 36 may be equipped with a force measuring device 37 or, instead of this device or in addition thereto, it may be equipped with a vertical force generating device for producing the above mentioned high frequency or relatively high frequency vertical force loads (not shown).

In addition, a longitudinal force generator 38 is coupled to each end of the vehicle axle 33 by way of a force transmitting rod 39 and joints 23. Further, a lateral force generator 40 is coupled to the lefthand or righthand wheel substitute 34, respectively, by way of a force transmitting rod 41 and joints 23. Lastly, a braking and driving force generator 42 is coupled to each of the two brake force transmitting levers 35, in each case by way of a force transmitting rod 43 and joints 23.

By these means, the commercial vehicle springs 16 (or only a single such spring) may be tested for strength with or without adjacent components such as the commercial vehicle axle, axle stubs, spring brackets, frame connections of the vehicles, or the like under the accidental loads corresponding to those occurring in commercial vehicles on the road. If the commercial vehicle springs 16 are to be tested on their own, a connection, in particular a rigid connection, is provided as a means for simultaneously coupling the wheel or wheel substitute 34 or the brake force transmitting lever 35 from each end of the axle 33 to a common lateral force generator or a common braking and driving force generator. The lateral force is in this case introduced into the longitudinal center of the rigid connection between the right and left wheel substitute 34 and the braking or driving force is introduced into the longitudinal, center of the rigid connection between the brake force transmitting levers 35, i.e. at a point corresponding to the longitundinal center of the vehicle axle 33. In that case only one longitudinal force generator need be used (not shown).

As further shown in FIG. 5, the points of connection 44 of the two vertical force generators 18 and 19 to the supporting assembly 20 are symmetrical with respect to the axis 25 of the pivot shaft 24. The vertical forces therefore act on the supporting assembly 20 in such a manner that when they act simultaneously they produce symmetrical compression of both vehicle springs 16 and when they act alternately they produce compression of one vehicle spring 16 and simultaneous expansion of the other spring 16.

The point of connection 44 of each vertical force generator 18 and 19 is situated on a line of action 45 of a commercial vehicle spring 16. This results in a short force path with efficient force utilization. The points of connection 44 may, however, also be situated adjacent to the lines of action 45 or in the region between the lines 45.

In the preferred embodiment of the apparatus shown in FIG. 5, the pivot shaft 24 is situated in the plane in which the vehicle springs are fixed to the assembly 20 when the assembly 20 is under a static load or load free, in particular the pivot shaft is then situated in the plane of the spring brackets 30. This height may be adjustable by designing the pivot shaft bearing 20c so that it is adjustable in the vertical direction relatively to the supporting assembly 20. This adjustability may in particular be so arranged that the pivot shaft can be adjusted to levels above or below the plane of the spring brackets 30 within a range of plus and minus the height of the load free vehicle springs 16.

By using original parts with original dimensions, the apparatus and the process according to the invention can be used for directly simulating the variations in load determined from measurements taken under driving conditions or synthetic variations in load, in particular the following types of load:

(a) Loads occurring when travelling forwards in a straight line, produced by quasi-static symmetrical vertical forces with superimposed alternating vertical forces by means of the vertical force generators 18 and 19 with or without lateral forces. In addition symmetrical and asymmetrical longitudinal forces such as occur from irregularities on the ground may be superimposed by means of the longitudinal force generators 38.

(b) Loads occurring during cornering, comprising left and right forces due to alternating vertical forces and lateral forces. At any one time, one side is subjected to high vertical forces and to lateral forces of corresponding magnitude directed towards the center of the vehicle while the other side is subjected to lower vertical forces and to lateral forces directed towards the outside of the vehicle.

(c) Loads occurring during braking and acceleration due to symmetrical vertical forces and rearwardly or forwardly directed braking or accelerating forces.

The process and the apparatus according to the present invention provide in their basic form and/or in their embodiment the following particular advantages:

(1) The commercial vehicle axle 33 remains under load, in particular under vertical force load parallel to the horizontal plane of the surface of the base 46 of the apparatus shown in FIGS. 5 and 6. The vertical forces therefore always act in the same direction, namely at right angles to the vehicle axle 33, regardless of the state of compression or expansion of the springs (or of only a single spring if the vehicle is constructed accordingly). Further, the direction of action of the lateral forces always remains parallel to the axle 33 of the vehicle independently of the degree of spring compression and expansion.

(2) Since the axle 33 of the vehicle is fixed in relation to the base 46 or horizontal plane, no coupling faults can occur due to the lateral, braking and longitudinal forces influencing each other.

(3) Since the supporting assembly 20 is guided by means of the vertical guide 27 and is rotatably mounted in the longitudinal axis by means of the pivot shaft 24, the spring excursions of compression and expansion are completely or at least for the most part taken up by the supporting assembly 20.

(4) Since the axis 25 of the pivot shaft is situated in the plane of attachment 30 of the spring to the supporting assembly 20, the number of spring movements per unit time is small and the spring excursions are vertical.

(5) Since the axle 33 of the commercial vehicle is supported in the horizontal plane (base 46) by means of a wheel substitute 34 at each axial end, the vehicle axle 33 remains positionally fixed in the vertical direction but with the possibility of lateral displacement.

(6) The vertical force generators 18 and 19 can produce symmetrical spring compression when operated simultaneously and compression of one vehicle spring 16 with concomitant expansion of the other vehicle spring 16 when operated alternately.

(7) A preload may be produced (corresponding to the weight of the car body of the vehicle) by simultaneous action on the vertical force generators 18 and 19, and a low frequency or relatively high frequency vertical, alternating compression of both vehicle springs 16 with a small spring excursion can be achieved by a superimposed alternating operation of the vertical force generators 18, 19.

(8) The forces of reaction are introduced into the steering knuckles and the vehicle axle 33 through the wheel substitute 34.

(9) Original parts may be used and two commercial vehicle springs 16 and adjacent components can be tested simultaneously.

(10) The geometrical relationships can be kept constant due to the use of original parts so that the forces measured at the point of contact of the wheel tread can be used directly for simulation and proof of strength. The spring deformations and excursions resembling those occurring on the road are then automatically obtained from the results. No geometrical corrections of any magnitude are required since the coupling errors are small and there is little mutual influence.

(11) The lateral force is introduced into the commercial vehicle axle 33 and the vehicle springs 16 by way of wheel substitute 34, in particular on the wheel substitute levers.

(12) The braking force and the accelerating force are each introduced by way of a braking and driving force generator 42 acting on the brake force transmitting lever 35.

(13) The longitudinal forces are introduced into the axle stub by two longitudinal force generators 38.

(14) Due to the arrangement of the vertical force generators 18, 19 on or close to the line of action of the commercial vehicle springs 16, the vertical forces are not required to move by an amount greater than the spring excursions.

(15) High frequency additional loads may be produced by providing two additional vertical force generators in place of the vertical supports 36. This arrangement enables slow movements, which are simulated by the vertical force generators 18 and 19, to be separated from rapid movements, which are brought about by the above mentioned additional vertical force generators provided in or instead of the vertical supports 36. A considerable reduction in the consumption of hydraulic power, oil and energy may thereby be achieved.

(16) Original wheels and tires of a commercial vehicle ma be tested in the apparatus by using these original wheels and tires in place of the wheel substitute 34.

(17) Helical springs or cushion type pneumatic springs or other springs may be tested as commercial vehicle springs 16 instead of leaf springs.

(18) Axles, steering knuckles, frames; spring attachment elements and the like may be tested, in particular in their original form.

(19) The apparatus according to the invention may also be used for testing one or more commercial vehicle springs alone.

(20) Lastly, the vertical, lateral, longitudinal and braking and driving forces introduced may be determined independently of one another by means of force measuring devices 37 such as are provided here for measuring the vertical force in the vertical support 36 (measurement of vertical restoring force). For measuring the lateral force, longitudinal force and the braking and driving force, these force measuring devices 37 are provided in the path of transmission of the respective force generator 40, 38 and 42 respectively, as shown in FIGS. 5 and 6.

It should be noted that the above mentioned static and low frequency or relatively low frequency vertical forces correspond to the weight of the commercial vehicle in the unladen or laden state and give rise to slow up and down movements of the commercial vehicle or its body at a frequency preferably below 5 Hz, mainly in the region of 2 Hz. The high frequency or relatively high frequency vertical forces, on the other hand, are additional loads produced by impacts due to irregularities in the ground and have frequencies of about 10 to 20 Hz or more, e.g. 20 to 30 Hz.

These high frequency and relatively high frequency vertical forces produce only small spring excursions of compression and expansion compared to those produced by static and low frequency or relatively low frequency vertical forces under simulation of conditions resembling those occurring in practice.

It should also be noted that the apparatus according to the invention may, if desired, be used only for testing one or more components adjacent to the spring(s) and/or axle of the commercial vehicle, even if the commercial vehicle axle and/or spring(s) is or are installed in the apparatus.

It should further be noted that the range of protection of the apparatus claims is not limited to the possibilities of use mentioned there but rather extends to all possibilities of using the apparatus.

We claim:

1. An apparatus for testing an axle assembly of a commercial vehicle, wherein said assembly includes at least an axle and springs and is subjected to testing under operational forces, including vertical operational forces, said apparatus comprising:
    axle support fixture means for supporting the axle of said axle assembly;
    a supporting assembly coupled to the springs of the axle assembly and effective for transferring the vertical operational forces to the axle assembly;

frame means including means for movably guiding said supporting assembly; and at least two high displacement, vertical force actuators coupled to said supporting assembly and effective for simulating the vertical operational forces and for applying the same to said supporting assembly.

2. An apparatus according to claim 1, further comprising lateral force actuators for simulating lateral operational forces, said lateral force actuators acting on said axle assembly via said axle support fixture means.

3. An apparatus according to claim 1, further comprising braking and accelerating force actuators for simulating braking and accelerating operational forces and for acting on a brake and accelerating force transmitting lever attached to said axle.

4. An apparatus according to claim 1, further comprising longitudinal force actuators for simulating longitudinal operational forces and for acting on an axle spindle of said axle.

5. An apparatus according to claim 1, further comprising additional vertical force actuators for simulating low displacement, high frequency operational forces, said additional, vertical force actuators being effective for acting on said supporting assembly for superimposing additional vertical forces over said vertical forces.

6. An apparatus according to claim 1, wherein said frame means comprises a pivot bearing for mounting said supporting assembly to said frame means in a manner enabling pivotal movement of said axle about a longitudinal axis.

7. An apparatus according to claim 6, wherein said longitudinal axis is arranged on a level corresponding to the mounting level of brackets of said springs.

8. An apparatus according to claim 6, wherein said frame means comprises a parallel guide means for enabling parallel displacement of said axle assembly.

9. An apparatus according to claim 8, wherein said longitudinal axis is arranged on a level corresponding to the mounting level of brackets of said springs.

10. An apparatus according to claim 1, wherein said frame means comprises a parallel guide means for enabling parallel displacement of said axle assembly.

11. An apparatus according to claim 1, wherein said axle is maintained in a substantially unchanged position in the vertical plane.

* * * * *